US009296787B2

(12) United States Patent
Kobayashi et al.

(10) Patent No.: US 9,296,787 B2
(45) Date of Patent: *Mar. 29, 2016

(54) ANTITUMOR PEPTIDE AND USE THEREOF

(71) Applicant: TOAGOSEI CO., LTD., Tokyo (JP)

(72) Inventors: Nahoko Kobayashi, Tsukuba (JP); Tetsuhiko Yoshida, Tsukuba (JP)

(73) Assignee: TOAGOSEI CO. LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/367,204

(22) PCT Filed: Dec. 20, 2012

(86) PCT No.: PCT/JP2012/083109
§ 371 (c)(1),
(2) Date: Jun. 19, 2014

(87) PCT Pub. No.: WO2013/094697
PCT Pub. Date: Jun. 27, 2013

(65) Prior Publication Data
US 2015/0018286 A1    Jan. 15, 2015

(30) Foreign Application Priority Data

Dec. 20, 2011  (JP) .................................. 2011-278973
Dec. 20, 2011  (JP) .................................. 2011-278974

(51) Int. Cl.
A61K 38/08    (2006.01)
A61K 38/10    (2006.01)
C07K 7/08     (2006.01)
C07K 7/06     (2006.01)
A61P 35/00    (2006.01)

(52) U.S. Cl.
CPC . *C07K 7/08* (2013.01); *A61K 38/08* (2013.01); *C07K 7/06* (2013.01)

(58) Field of Classification Search
CPC ............. A61K 38/08; C07K 7/08; C07K 7/06
See application file for complete search history.

(56) References Cited

U.S. PATENT DOCUMENTS

| | | | | |
|---|---|---|---|---|
| 5,595,756 A * | 1/1997 | Bally et al. | | 424/450 |
| 6,344,443 B1 * | 2/2002 | Liu et al. | | 514/20.6 |
| 2007/0021347 A1 | 1/2007 | Khan et al. | | |
| 2010/0297758 A1 | 11/2010 | Yoshida et al. | | |
| 2012/0122225 A1 | 5/2012 | Kobayashi et al. | | |
| 2012/0149053 A1 | 6/2012 | Yoshida et al. | | |
| 2013/0323776 A1 | 12/2013 | Yoshida et al. | | |
| 2015/0018286 A1 | 1/2015 | Kobayashi et al. | | |

FOREIGN PATENT DOCUMENTS

| CN | 1763082 A | * | 4/2006 | ............... C07K 7/08 |
|---|---|---|---|---|
| DE | 102009021681 A1 | | 11/2010 | |
| WO | 03024408 A2 | | 3/2003 | |
| WO | 03037172 A2 | | 5/2003 | |
| WO | 2004005472 A2 | | 1/2004 | |
| WO | WO 2004/020457 A2 | * | 3/2004 | |
| WO | WO 2007/004869 A2 | | 1/2007 | |
| WO | 2007056188 A1 | | 5/2007 | |
| WO | WO 2008/081812 A1 | | 7/2008 | |
| WO | WO 2009/093692 A1 | | 7/2009 | |
| WO | WO 2011/013698 A1 | | 2/2011 | |
| WO | WO 2011/013699 A1 | | 2/2011 | |

OTHER PUBLICATIONS

Sporn, B and Suh, N, Chemoprevention of cancer, Carcinogenesis, 2000, 21, pp. 525-530.*
Machine translation of CN 1763082 A, pp. 1-29, accessed May 27, 2015.*
Ito et al, Co-culture of human breast adenocarcinoma MCF-7 cells and human dermal fibroblasts enhances the production of matrix metalloproteinases 1, 2 and 3 in fibroblasts, British Journal of Cancer, 1995, 71, pp. 1039-1045.*
Raderschall et al, Elevated Levels of Rad51 Recombination Protein in Tumor Cells, Cancer Research, 2002, 62, pp. 219-225.*
Cancer Drug Design and Discovery. Neidle, Stephen, ed., Elsevier/ACademic Press, 2008, p. 427-431.*
Cellular and Molecular Basis of Cancer-Merck Manual, from http://www.merckmanuals.com/professional/print/hematology_and_oncology/overview_of . . . , pp. 1-5, accessed May 10, 2012.*
Rudinger, Peptide Hormones, JA Parsons, Ed., 1976, pp. 1-7.*
SIGMA, 2004, pp. 1-2.*
Berendsen, A Glimpse of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Paradis-Bleau et al., "Peptide inhibitors of the essential cell division protein FtsA", *Protein Engineering, Design & Selection*, 2005, pp. 85-91, vol. 18, No. 2, Oxford University Press.
Paradis-Bleau et al., "Identification of *Pseudomonas aeruginosa* FtsZ peptide inhibitors as a tool for development of novel antimicrobials", *Journal of Antimicrobial Chemotherapy*, Jun. 2004, pp. 278-280.

(Continued)

*Primary Examiner* — Julie Ha
*Assistant Examiner* — Li Ni Komatsu
(74) *Attorney, Agent, or Firm* — Oliff PLC

(57) ABSTRACT

This invention provides an antitumor peptide and an antitumor composition that includes the peptide for suppressing proliferation of at least one species of tumor cells. The antitumor composition provided by this invention includes an antitumor peptide capable of inducing formation of multipolar spindles in at least one species of tumor cells, and at least one species of pharmaceutically acceptable carrier, wherein the antitumor peptide is a synthetic peptide having an amino acid sequence selected from SEQ ID NOs: 1 to 22 or an amino acid sequence formed by substituting, deleting and/or adding one, two or three amino acid residues in/from/to the selected amino acid sequence.

2 Claims, 6 Drawing Sheets

(56) References Cited

OTHER PUBLICATIONS

Vollmer, "The prokaryotic cytoskeleton: a putative target for inhibitors and antibiotics?", *Appl Microbiol Biotechnol*, 2006, pp. 37-47, vol. 73.

Huang et al., "Targeting FtsZ for anti-tuberculosis drug discovery: non-cytotoxic taxanes as novel anti-tuberculosis agents", *J Med Chem.*, Jan. 26, 2006, vol. 49, No. 2.

International Search Report issued in International Patent Application No. PCT/JP2012/083109 mailed Mar. 12, 2013.

May 29, 2015 Extended European Search Report issued in European Patent Application No. 12860097.0.

Läppchen et al., "Probing FtsZ and Tubulin with C8-Substituted GTP Analogs Reveals Differences in Their Nucleotide Binding Sites," *Chemistry & Biology*, vol. 15, pp. 189-199, Feb. 2008.

Ojima et al., "Drug discovery targeting cell division proteins, microtubules and FtsZ," *Bioorganic & Medicinal Chemistry*, vol. 22, pp. 5060-5077, 2014.

Cho et al., "Depletion of CPAP by RNAi disrupts centrosome integrity and induces multipolar spindles," *Biochemical and Biophysical Reasearch Communications*, vol. 339, pp. 742-747, 2006.

Sakaushi et al., "Live imaging of spindle pole disorganization in docetaxel-treated multicolor cells," *Biochemical and Biophysical Research Communications*, vol. 357, pp. 655-660, 2007.

Jaiswal et al., "9-Bromonoscapine-induced mitotic arrest of cigarette smoke condensate-transformed breast epithelial cells," *J Cell Biochem*, 106(6), pp. 1-20, Apr. 15, 2009.

Jul. 3, 2014 International Preliminary Report on Patentability issued in International Patent Applicaton No. PCT/JP2012/083110.

Jun. 18, 2015 Office Action issued in U.S. Appl. No. 14/366,971.

Jul. 3, 2014 International Preliminary Report on Patentability issued in International Patent Application No. PCT/JP2012/083111.

Jun. 23, 2015 Office Action issued in U.S. Appl. No. 14/367,023.

U.S. Appl. No. 14/366,971, filed Jun. 19, 2014 in the name of Nahoko Kobayashi et al.

U.S. Appl. No. 14/367,023, filed Jun. 19, 2014 in the name of Nahoko Kobayashi et al.

Jan. 29, 2013 International Search Report issued in International Patent Application No. PCT/JP2012/083110.

Jan. 29, 2013 International Search Report issued in International Patent Application No. PCT/JP2012/083111.

\* cited by examiner

ANTITUMOR PEPTIDE AND USE THEREOF

TECHNICAL FIELD

The present invention relates to an artificially synthesized antitumor peptide capable of suppressing proliferation of tumor cells (cancer cells) and the use thereof.

The present application claims priority based on Japanese Patent Application No. 2011-278973 and Japanese Patent Application No. 2011-278974 filed on Dec. 20, 2011, and their entire contents are incorporated herein by reference.

BACKGROUND ART

One of the characteristics of tumor cells (cancer cells) is that as compared to normal cells, they undergo rapid cell division, resulting in a significantly high cell proliferation rate. Thus, many anticancer agents to kill tumor cells or to inhibit their proliferation are drugs that inhibit division of tumor cells (cancer cells). For example, alkylating agents are drugs that act on the DNA of tumor cells (cancer cells) to crosslink the bases between double strands, thereby inhibiting DNA replication and blocking cell division. Antimetabolites such as 5-FU, etc., are drugs that inhibit DNA synthesis and block cell division.

As for such a drug (anticancer agent) to inhibit rapid division of tumor cells (cancer cells), expectations are building for development of a drug formulated with a physiologically active peptide having a relatively small number of amino acid residues and a low molecular weight. As compared to anticancer drugs formulated with conventional chemical substances, drugs formulated with physiologically active peptides are expected to reduce side effects while they are also expected to act solely on specific target cells (cancer cells). For example, Patent Document 1 and Patent Document 2 disclose antitumor peptides (anticancer peptides) that are as short as 50 or fewer amino acid residues.

CITATION LIST

Patent Literature

[Patent Document 1] WO 2008/081812A
[Patent Document 2] WO 2007/004869A
[Patent Document 3] WO 2009/093692A
[Patent Document 4] WO 2011/013698A
[Patent Document 5] WO 2011/013699A

Non-Patent Literature

[Non-Patent Document 1] Protein Engineering, Design & Selection, vol. 18(2), 2005, pp. 85-91
[Non-Patent Document 2] Journal of Antimicrobial Chemotherapy, vol. 54(1), 2004, pp. 278-280

SUMMARY OF INVENTION

The present invention was made to provide a novel antitumor (anticancer) peptide that acts by a different mechanism from heretofore antitumor peptides as those disclosed in the aforementioned patent documents as well as an antitumor composition (anticancer composition) for suppressing proliferation of at least one species of tumor cells, with the composition comprising the peptide as a component.

The present inventors have focused on several peptides reported in Non-Patent Document 1 and Non-Patent Document 2. More specifically, as for peptides to inhibit the activity of the FtsZ (Filamenting temperature-sensitive mutant Z) protein which is present in bacteria (which are prokaryotes) and forms a protein assembly called the Z ring involved in bacterial cell division or for peptides to inhibit the activity of the FtsA (Filamenting temperature-sensitive mutant A) protein known to work as an anchor to bind the FtsZ protein to cell membranes when coupled to the C-terminus of the FtsZ protein (i.e. for peptides that inhibit the GTPase activity of the FtsZ protein or the ATPase activity of the FtsA protein), they have focused on several peptides (i.e. peptides capable of acting as FtsZ inhibitors or FtsA inhibitors) isolated by employing a general phage display technique.

The present inventors have found out that when these peptides capable of acting as FtsZ inhibitors or FtsA inhibitors are supplied to various species of tumor cells (cancer cells), multipolar spindles, instead of normal bipolar spindles, can be frequently formed in the tumor cells; in other words, many centrosomes (including fragments of pericentriolar materials (PCM); the same applies hereinafter) can be present dispersed in a cell unlike the way dipolar spindles are formed, a spindle (multipolar spindle) randomly extending from the many respective dispersed centrosomes serving as spindle poles can be formed.

They have further confirmed that induction of formation of such multipolar spindles (or simply "multipolarity induction" hereinafter) can inhibit normal cell division to block or suppress proliferation of target (subject) tumor cells (cancer cells), whereby the present invention has been completed.

In the present description, the term "tumor cells" is equivalent to "cancer cells", with the term being used to distinguish them from normal cells that have not yet become cancerous (malignant).

In order to accomplish the objective, the present invention provides a composition as described below. Namely, an embodiment of the composition disclosed herein is a composition for suppressing proliferation of at least one species of tumor cells, with the composition comprising an antitumor peptide capable of inducing formation of multipolar spindles in the at least one species of tumor cells, and further comprising at least one species of pharmaceutically acceptable carrier.

The composition is characterized by comprising, as the antitumor peptide, a synthetic peptide consisting of an amino acid sequence selected from the following amino acid sequences that act as FtsZ inhibitors or FtsA inhibitors:

(1) CSSATGKSC, (SEQ ID NO: 1)

(2) CLAPSPSKC, (SEQ ID NO: 2)

(3) CLGQTKMRC, (SEQ ID NO: 3)

(4) CGHRPYQYC, (SEQ ID NO: 4)

(5) CWAFPLHHC, (SEQ ID NO: 5)

(6) CTLNSHSNC, (SEQ ID NO: 6)

(7) CEISAKRTC, (SEQ ID NO: 7)

(8) CHILHAQAC, (SEQ ID NO: 8)

-continued

```
                                    (SEQ ID NO: 9)
(9)  CPRPPSLEC, (SEQ ID NO: 10)
(10) CTGHWASEC, (SEQ ID NO: 11)
(11) CSYEKRPMC, (SEQ ID NO: 12)
(12) CLTKSYTSC, (SEQ ID NO: 13)
(13) SVSVGMKPSPRP, (SEQ ID NO: 14)
(14) FTTSNHTSRHGS, (SEQ ID NO: 15)
(15) TPSLPPTMFRLT, (SEQ ID NO: 16)
(16) GPHHYWYHLRLP, (SEQ ID NO: 17)
(17) QSPVNHHYHYHI, (SEQ ID NO: 18)
(18) NMTTYPMHNNTV, (SEQ ID NO: 19)
(19) SLLPHSNHAKHY, (SEQ ID NO: 20)
(20) EFEYFHPATFRL, (SEQ ID NO: 21)
(21) GPHLGMNQRRRP
and (SEQ ID NO: 22)
(22) GAVTYSRISGQY;
``` or an amino acid sequence formed by substituting, deleting and/or adding one, two or three amino acid residues in/from/to the selected amino acid sequence.

According to such a composition, as a result of the inclusion of a synthetic peptide (antitumor peptide) having the aforementioned amino acid sequence, by supplying the composition (the antitumor peptide) to a target (subject) tumor (i.e. tumor cells constituting the tumor tissue), 3 or more (typically 5 or more, preferably 8 or more) centrosomes can be formed in the tumor cells (typically M-phase cells) constituting the tissue and formation of multipolar spindles having those several centrosomes serving as spindle poles can be induced. This inhibits division of cells (multipolar cells) having multipolar spindles formed therein and, as a result, proliferation of the tumor cells can be blocked or suppressed.

Another preferable embodiment of the composition disclosed herein is a composition for suppressing proliferation of at least one species of tumor cells, with the composition comprising an antitumor peptide capable of inducing multipolarity in the at least one species of tumor cells, and further comprising at least one species of pharmaceutically acceptable carrier.

The composition is characterized by comprising, as the antitumor peptide, a synthetic peptide consisting of an amino acid sequence selected from the following amino acid sequences that act as FtsZ inhibitors or FtsA inhibitors:

```
                                    (SEQ ID NO: 1)
(1)  CSSATGKSC, (SEQ ID NO: 2)
(2)  CLAPSPSKC, (SEQ ID NO: 3)
(3)  CLGQTKMRC, (SEQ ID NO: 4)
(4)  CGHRPYQYC, (SEQ ID NO: 5)
(5)  CWAFPLHHC, (SEQ ID NO: 6)
(6)  CTLNSHSNC, (SEQ ID NO: 7)
(7)  CEISAKRTC, (SEQ ID NO: 8)
(8)  CHILHAQAC, (SEQ ID NO: 9)
(9)  CPRPPSLEC, (SEQ ID NO: 10)
(10) CTGHWASEC, (SEQ ID NO: 11)
(11) CSYEKRPMC, (SEQ ID NO: 12)
(12) CLTKSYTSC, (SEQ ID NO: 13)
(13) SVSVGMKPSPRP, (SEQ ID NO: 14)
(14) FTTSNHTSRHGS, (SEQ ID NO: 15)
(15) TPSLPPTMFRLT, (SEQ ID NO: 16)
(16) GPHHYWYHLRLP, (SEQ ID NO: 17)
(17) QSPVNHHYHYHI, (SEQ ID NO: 18)
(18) NMTTYPMHNNTV, (SEQ ID NO: 19)
(19) SLLPHSNHAKHY, (SEQ ID NO: 20)
(20) EFEYFHPATFRL, (SEQ ID NO: 21)
(21) GPHLGMNQRRRP
and (SEQ ID NO: 22)
(22) GAVTYSRISGQY;
``` or an amino acid sequence formed by substituting, deleting and/or adding one, two or three amino acid residues in/from/to the selected amino acid sequence; and also an amino acid sequence that constitutes a nucleolar localization signal (NoLS) and is selected from SEQ ID NO: 23 to SEQ ID NO: 30, or an amino acid sequence formed by substituting, deleting and/or adding one, two or three amino acid residues in/from/to the selected amino acid sequence.

The present inventors have found out that amino acid sequences known as nucleolar localization signals (NoLS) (see Patent Documents 3, 4 and 5) are involved in transporting peptides from the extracellular space into nuclei (typically nucleoli). By the use of a synthetic peptide constituted to include the amino acid sequence (i.e. an NoLS-coupled antitumor peptide), the antitumor peptide can be introduced more efficiently into target tumor tissue (tumor cells). Thus, the use of the composition (antitumor peptide) in the present embodiment will increase the productivity of multipolar cells and allow for more efficient blocking or suppression of tumor cell proliferation.

The present invention provides a method for suppressing proliferation of at least one species of tumor cells, the method characterized by supplying a composition disclosed herein to target tumor cells (e.g. in vitro or in vivo) at least once.

According to such a method, by supplying tumor cells with a synthetic peptide (antitumor peptide) consisting of one of the amino acids described above, multipolarity can be induced in the tumor cells to inhibit cell division; and as a result, proliferation of the target tumor cells (tumor, cancer tissue) can be blocked or suppressed.

In a preferable embodiment, the method disclosed herein allows for efficient suppression of proliferation of tumor cells forming a squamous cell carcinoma or tumor cells forming an adenocarcinoma.

DESCRIPTION OF EMBODIMENTS

Figure 1:
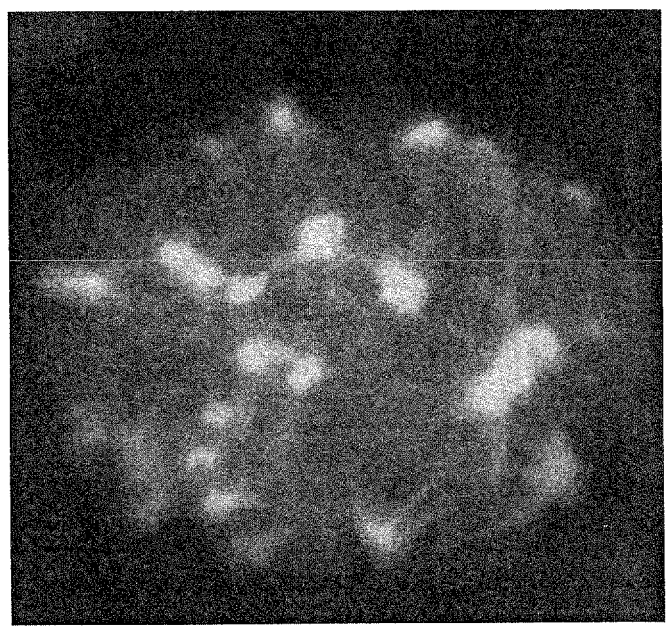
FIG. 1 is a fluorescence microscope photo (image) showing the state of a cultured cell after 24 hours of incubation following addition of a sample peptide (Sample 1) to a culture medium of HeLa cells to a peptide concentration in the culture medium of 50 µM, with the photo being a merged image of a DAPI nuclear stain image and a fluorescence image showing the result of an immunofluorescence assay using a fluorescence-labeled anti-tubulin antibody.

Preferred embodiments of the present invention are described below. Note that technical matters other than the matters particularly mentioned in the present description (e.g. primary structures of antitumor peptides disclosed herein) which are required for carrying out the present invention (e.g., general matters relating to chemical peptide synthesis, cell cultivation, and preparation of a pharmaceutical composition containing a peptide) are matters of design variation that could be apprehended by a person skilled in the art based on conventional art in such fields as cell engineering, physiology, medicine, pharmacology, organic chemistry, biochemistry, genetic engineering, protein engineering, molecular biology, genetics, and the like. The present invention can be practiced based on the technical details disclosed in the present description and common general technical knowledge in the pertinent fields. In the following description, amino acids are indicated by single-letter designations (in sequence listings, by three-letter designations) in accordance with the nomenclature for amino acids set forth in the IUPAC-IUB guidelines.

The present description incorporates by reference the entire contents of all the documents cited herein.

In the present description, the term "synthetic peptide" refers to a peptide fragment that is manufactured by artificial chemical synthesis or biosynthesis (i.e. genetic engineering-based production).

In this description, the term "peptide" refers to an amino acid polymer having a plurality of peptide bonds, and is not limited by the number of amino acid residues included in the peptide chain, with the term typically referring to one having a relatively small molecular weight with a total of no more than 50 (e.g. no more than 30) amino acid residues.

In this description, unless otherwise specified, the term "amino acid residue" includes the N-terminal amino acid and the C-terminal amino acid of a peptide chain.

In this description, the term "tumor" should be interpreted in a broad sense and refers to general tumors (typically malignant tumors) including carcinomas and sarcomas as well as lesions of blood and hematopoietic tissue (leukemia, lymphoma, etc.). The term "tumor cells" refers to cells that form such a tumor, typically referring to cells that have come to undergo abnormal proliferation with no relation to surrounding normal tissue (i.e. cells that have become cancerous). Thus, unless otherwise specified, cells classified as tumor cells (cancer cells) instead of normal cells are called as tumor cells regardless of the origin and nature of the cells. The concept of tumor cells referred to herein encompasses cells that form epithelial tumors (squamous cells carcinoma, adenocarcinoma, etc.), nonepithelial tumors (various types of sarcoma, osteosarcoma, etc.), various types of cytoma (neuroblastoma, retinoblastoma, etc.), lymphomas, melanomas, and so on.

In this description, the term "modified amino acid sequence" regarding a certain amino acid sequence refers to an amino acid sequence formed by substituting, deleting and/or adding (inserting) one or several (e.g. two or three) amino acid residues without impairing the function of the certain amino acid sequence (e.g. the ability of the antitumor peptides to induce multipolarity, the NoLS's transportability from the extracellular space into nuclei). Typical examples of the modified amino acid sequence referred to in the present description include a sequence generated by conservative amino acid replacement where one or several (typically two or three) amino acid residues are conservatively substituted (e.g., a sequence where a basic amino acid residue has been substituted with a different basic amino acid residue; e.g. mutual substitution between a lysine residue and an arginine residue), a sequence obtained by adding (inserting) or deleting one or several (typically two or three) amino acid residues in a certain amino acid sequence, and the like. Thus, the antitumor peptide disclosed herein encompasses synthetic peptides consisting of amino acid sequences identical to the amino acid sequences of the respective SEQ ID NOs as well as a synthetic peptide consisting of an amino acid sequence resulting from substitution (e.g. the conservative substitution), deletion and/or addition of one or several (typically two or three) amino acid residues in/from/to the amino acid sequence of each SEQ ID NO while showing comparable multipolarity-inducing activity.

In this description, the term "polynucleotide" refers to a polymer (nucleic acids) in which several nucleotides are linked by phosphodiester bonds, but not limited by the number of nucleotides. The polynucleotide in the present description encompasses DNA fragments and RNA fragments of various lengths. The term "artificially designed polynucleotide" refers to a polynucleotide whose chain (the whole length) does not exist by itself in nature and that is manufactured artificially by chemical synthesis or biosynthesis (i.e., genetic engineering-based production).

The composition disclosed herein is a composition (or sometimes referred to as an "antitumor composition" hereinafter) for suppressing proliferation of tumor cells, with the composition comprising, as an active ingredient, an antitumor peptide consisting of an amino acid sequence which has been found for the first time by the present inventors to have an activity to induce multipolarity in certain tumor cells as described earlier or an NoLS-coupled antitumor peptide constituted by coupling an NoLS to the N-terminus or the C-terminus of the amino acid sequence of the peptide. It is also referred to as a proliferation inhibitor of tumor cells.

Some of the antitumor peptides disclosed herein are each constituted with an amino acid sequence represented by one of SEQ ID NO: 1 to SEQ ID NO: 22 (or a modified sequence thereof). As described earlier, the peptides consisting of these amino acid sequences can act as FtsA inhibitors (SEQ ID NOs: 1 to 10, 13 to 21) or FtsZ inhibitors (SEQ ID NOs: 11 to 12, 22) against certain species of bacteria as reported in Non-Patent Document 1 or Non-Patent Document 2 listed earlier. Heretofore, however, such various peptides capable of acting as FtsA inhibitors or FtsZ inhibitors have never been known to induce multipolarity in tumor cells (eukaryotic cells), or nothing has ever suggested this, either.

Some others of the antitumor peptides disclosed herein are each constituted with an amino acid sequence represented by one of SEQ ID NO: 1 to SEQ ID NO: 22 (or a modified sequence thereof) as well as an amino acid sequence forming an NoLS represented by one of the following SEQ ID NO: 23 to SEQ ID NO: 30 (or a modified sequence thereof):

(23) KKRTLRKNDRKKR, (SEQ ID NO: 23)

(24) WRRQARFK, (SEQ ID NO: 24)

(25) RSRKYTSWYVALKR, (SEQ ID NO: 25)

(26) MAKSIRSKHRRQMRMMKRE, (SEQ ID NO: 26)

(27) MARRRRHRGPRRPRPP, (SEQ ID NO: 27)

(28) GRCRRLANFGPRKRRRRRR, (SEQ ID NO: 28)

(29) RRRKRNRDARRRRRKQ (SEQ ID NO: 29)
and

(30) MQRKPTIRRKNLRLRRK. (SEQ ID NO: 30)

These amino acid sequences listed are all known as NoLS, and their data can be obtained, for example, from the database of amino acid sequences of protein provided by NCBI (National Center for Biotechnology Information).

Namely, the amino acid sequence of SEQ ID NO: 23 corresponds to an NoLS consisting of 13 amino acid residues from amino acid residue 491 to amino acid residue 503 of LIM kinase 2 present in human endothelial cells, which is a type of protein kinase involved in intracellular signal transduction.

The amino acid sequence of SEQ ID NO: 24 corresponds to an NoLS consisting of 8 amino acid residues contained in the N protein (nucleocapsid protein) of IBV (avian infectious bronchitis virus) which belongs to the genus *Coronavirus*.

The amino acid sequence of SEQ ID NO: 25 corresponds to an NoLS consisting of 14 total amino acid residues originating from FGF2 (fibroblast growth factor 2).

The amino acid sequence of SEQ ID NO: 26 corresponds to an NoLS consisting of 19 total amino acid residues originating from a species of nucleolar protein (ApLLP).

The amino acid sequence of SEQ ID NO: 27 corresponds to an NoLS consisting of 16 total amino acid residues originating from a protein (γ(1)34.5) of HSV-1 (herpes simplex virus type 1).

The amino acid sequence of SEQ ID NO: 28 corresponds to an NoLS consisting of 19 total amino acid residues originating from p40 protein of HIC (human I-mfa domain-containing protein).

The amino acid sequence of SEQ ID NO: 29 corresponds to an NoLS consisting of 16 total amino acid residues originating from MEQ protein of MDV (Marek's disease virus).

The amino acid sequence of SEQ ID NO: 30 corresponds to an NoLS consisting of 17 total amino acid residues originating from survivin-deltaEx3 which is an apoptosis-suppressing protein.

By placing the NoLS species represented by one of these SEQ ID NOs on the N-terminal side or the C-terminal side of the amino acid sequence represented by one of SEQ ID NO: 1 to SEQ ID NO: 22 (or a modified sequence thereof), a preferable antitumor peptide (synthetic peptide) can be constituted.

The antitumor peptide disclosed herein preferably has at least one amidated amino acid residue. Amidation of a carboxyl group in an amino acid residue (typically the C-terminal amino acid residue of the peptide chain) may increase the structural stability (e.g., protease resistance) of the synthetic peptide.

The antitumor peptide disclosed herein is short in the chain length, having a relatively small number of amino acid residues (typically 30 or fewer). Thus, its chemical synthesis is facile and the antitumor peptide can be easily provided. With respect to the conformation (spatial structure) of the peptide, there are no particular limitations as long as it exhibits antitumor activity (i.e. activity to induce the multipolarity and inhibit or suppress cell division and also cell proliferation) in the environment for the use (in vitro or in vivo). From the standpoint of unlikeliness to become an immunogen (antigen), a preferable peptide has a linear or a helical structure. Peptides having these conformations are less likely to form epitopes. From such a standpoint, it is preferable as a peptide used for manufacturing a composition (antitumor drug) disclosed herein which is used for suppressing proliferation of at least one species of tumor cells.

It is noted that in the antitumor peptide disclosed herein, all amino acid residues are preferably L-amino acids while for as long as the multipolarity-inducing activity is not lost, part or all of the amino acid residues may be substituted with D-amino acids.

The antitumor peptide disclosed herein can be easily manufactured according to general chemical synthesis methodologies. For instance, any of conventional solid-phase and liquid-phase synthetic methods can be employed. A preferable solid-phase synthetic method uses Boc (t-butyloxycarbonyl) or Fmoc (9-fluorenylmethoxycarbonyl) as the protecting group for the amino group.

For the antitumor peptide disclosed herein, a peptide chain having a desired amino acid sequence and a portion with modification (e.g., C-terminal amidation, etc.) can be synthesized by solid-phase synthesis using a commercial peptide synthesizer (which is, for instance, available from PerSeptive Biosystems, Applied Biosystems, etc.).

Alternatively, the antitumor peptide may be biosynthesized based on genetic engineering techniques. In particular, a polynucleotide (typically a DNA strand) is synthesized so as to have a nucleotide sequence (including the ATG initiation codon) encoding the amino acid sequence of the desired antitumor peptide. Then, in accordance with the host cells, a recombinant vector is constructed so as to have an expression gene construct composed of the synthesized polynucleotide (DNA) and various regulatory elements (including promoters, ribosome binding sites, terminators, enhancers, and various cis-elements which control the expression level) to allow expression of the amino acid sequence within the host cells.

By an ordinary technique, this recombinant vector is inserted into prescribed host cells (e.g. yeasts, insect cells, plant cells), and the host cells, or tissue or a mass containing these cells are cultured under specific conditions. In this way, the target peptide can be expressed and produced intracellularly. The target antitumor peptide can be obtained by isolating the peptide from the host cells (from the culture medium if secreted), subjecting it to refolding and purification, and so on as necessary.

Methods hitherto used in the art may be directly employed without modification as the method for constructing the recombinant vector, introducing the constructed recombinant vector into the host cell, and so on. Because such methods themselves are not distinctive to the present invention, detailed description is omitted here.

For example, a fusion protein expression system may be employed to allow efficient large-scale production in host cells. In particular, a gene (DNA) coding for the amino acid sequence of the antitumor peptide of interest is chemically synthesized, and the synthesized gene is introduced to a preferred site on a suitable fusion protein expression vector (e.g. GST (glutathione S-transferase) fusion protein expression vectors such as the pET series available from Novagen as well as the pGEX series available from Amersham Bioscience). Host cells (typically, *Escherichia coli*) are then transformed by the vector. The resulting transformant is cultured to produce the target fusion protein. This protein is then extracted and purified. Subsequently, the purified fusion protein is cleaved with a specific enzyme (protease), and the liberated target peptide fragments (the designed antitumor peptide) are collected by a method such as affinity chromatography. As necessary, it is allowed to refold by a suitable method. The antitumor peptide disclosed herein can be produced by using such a fusion protein expression system heretofore known (e.g., the GST/His system available from Amersham Bioscience may be used).

Alternatively, the target polypeptide may be synthesized in vitro by constructing a template DNA for a cell-free protein synthesis system (i.e., a synthesized gene fragment having a nucleotide sequence that codes for the amino acid sequence of the antitumor peptide), and employing a cell-free protein synthesis system with use of various compounds (e.g., ATP, RNA polymerase, amino acids, etc.) required for the peptide synthesis. For information concerning cell-free protein synthesis systems, reference may be made to, for example, Shimizu et al., *Nature Biotechnology*, 19, 751-755 (2001), and Madin et al., *Proc. Natl. Acad. Sci. USA*, 97(2), 559-564 (2000). Based on the technology described in these articles, many corporations have been conducting contract manufacturing of polypeptides at the time when this application was filed. Also, wheat germ cell-free protein synthesis kits (such as PROTEIOS™ available from Toyobo Co., Ltd. of Japan) are commercially available.

A heretofore known method can be employed for facile production (synthesis) of a single-stranded or double-stranded polynucleotide containing a nucleotide sequence encoding the antitumor peptide disclosed herein and/or a nucleotide sequence complementary thereto. In other words, by selecting a codon corresponding to the respective amino acid residues constituting the designed amino acid sequence, a nucleotide sequence corresponding to the amino acid sequence of the antitumor peptide can be easily determined and provided. Once the nucleotide sequence is determined, by utilizing a DNA synthesizer, etc., can be easily obtained a polynucleotide (single strand) corresponding to the desired nucleotide sequence. Furthermore, the target double-stranded DNA can be obtained by using the resulting single-stranded DNA as a template and employing various enzymatic synthetic methods (typically PCR). The polynucleotide may be in the form of DNA or RNA (mRNA, etc.). The DNA can be provided as a double strand or a single strand. When it is provided as a single strand, it may be a coding strand (sense strand) or an anticoding strand (anti-sense strand) complementary thereto.

The polynucleotide obtained in such a way can be used as a material for constructing a recombinant DNA (expression cassette) for producing the antitumor peptide in various host cells or in a cell-free protein synthesis system.

The antitumor peptide disclosed herein can act on at least one species of tumor cells, cause formation of many centrosomes (typically, 3 or more, preferably 5 or more, particularly preferably 8 or more, even more preferably 10 or more, e.g. about 3 to 20 centrosomes per cell) in the tumor cells (typically in the M phase), and induce formation of a corresponding number of multipolar spindles. Such formation of multipolar spindles can inhibit normal cell division and lead to death of the tumor cells without proliferation. Thus, it can be preferably used as an active ingredient in a composition (i.e. a pharmaceutical composition such as an antitumor drug, etc.) used to suppress (or inhibit) proliferation of tumor cells. The antitumor peptide may be in a salt form as far as the multipolarity-inducing activity is not impaired. For example, it is possible to use an acid salt of the peptide, which can be obtained by adding a commonly used inorganic or organic acid in accordance with an ordinary technique. Alternatively, while the multipolarity-inducing activity is maintained, a different type of salt (e.g., a metal salt) can be used. Accordingly, the scope of the "peptide" described in this description and in claims encompasses such salt forms.

The antitumor composition disclosed herein may contain various pharmaceutically (medically) acceptable carriers in accordance with the preparation, as far as it can preserve the antitumor peptide which is active ingredient without losing its ability to induce the multipolarity. For example, carriers generally used as diluents or excipients in peptide medications can be utilized.

Although the carrier may suitably vary depending on the intended purpose and form of the composition disclosed herein (i.e. an antitumor composition), typical examples include water, physiological buffers and various organic solvents. The carrier may be an aqueous alcohol (ethanol or the like) solution at an appropriate concentration, glycerol, or non-drying oil such as olive oil. Alternatively, it may be a liposome. Examples of secondary ingredients that may be contained in the antitumor composition include various fillers, bulking agents, binders, wetting agents, surfactants, dyes, fragrances and the like.

Typical examples of the form of the antitumor composition (antitumor drug) include liquid formulations, suspensions, emulsions, aerosols, foams, granules, powders, tablets, capsules, ointments, aqueous gels and the like. For injection, etc., the antitumor composition may be formulated as a freeze-dried product or pellets to prepare a drug solution by dissolving in saline or a suitable buffer (e.g., PBS) just prior to use.

The process itself of preparing a composition (drug) in various forms with the antitumor peptide (primary ingredient) and various carriers (secondary ingredients) may be carried out in accordance with a heretofore known method. Because such a preparation process itself is not distinctive to the present invention, detailed description is omitted here. The detail information regarding formulations can be found in, for example, *Comprehensive Medicinal Chemistry*, edited by Corwin Hansch and published by Pergamon Press (1990). The entire contents of this book are incorporated in this description by reference.

The target cells to which the antitumor composition (antitumor peptide) disclosed herein is applied are not particularly limited as long as they are tumor cells (cancer cells) and are susceptible to multipolarity induction. The composition can be applied to various types of tumor cells occurring in humans or nonhuman mammals. Examples include cells forming squamous cell carcinomas, cells forming adenocarcinomas, and cells forming cytomas such as neuroblastomas, retinoblastomas, pheochromocytomas, and other cytomas.

Similarly to conventional peptide drugs, the antitumor composition disclosed herein can be used according to a method and a dosage that are appropriate to the preparation and intended purpose. For example, as a liquid formulation, it can be administered in a desired amount to an affected area (typically malignant tumor tissue) of a patient (i.e. living organism) by an intravenous, intramuscular, subcutaneous, intradermal or intraperitoneal injection. Alternatively, a solid formulation such as pills, or a gel or aqueous jelly-like formulation such as ointment, etc., can be administered directly to prescribed tissue (i.e. an affected area such as an organ or tissue containing tumor cells). Alternatively, a solid formulation such as pills can be administered orally. For oral administration, to suppress decomposition by digestive enzymes in digestive organs, encapsulation or application of a protective material (coating) is preferable.

Alternatively, for tumor cells (including a cell aggregation, tissue or an organ removed from a living organism) being cultured in vitro, the antitumor composition disclosed herein may be supplied in a suitable dose (i.e. a suitable dose of the antitumor peptide) to a medium of the target cultured cells (tissue, etc.).

The amount of the peptide per dose and the number of doses are not particularly limited as they may vary in accordance with conditions such as the type of tumor cells to be cultured, cell density (cell density at the incubation start), passage number, incubation conditions, type of culture medium, and so on. It is preferably supplied in one to several doses so that the concentration of the antitumor peptide in the culture medium is within a range of about 20 μM to 200 μM or preferably within a range of 50 μM to 100 μM.

Several worked examples relating to the present invention are described below while these examples are not intended to limit the scope of the invention.

EXAMPLE 1

Peptide Synthesis

A total of 44 different synthetic peptides consisting of the respective amino acid sequences shown in Tables 1 and 2 were produced using a peptide synthesizer described later. In the following description, the 44 in total of different peptides synthesized are referred to as Samples 1 to 44.

TABLE 1

| Sample No. | Amino acid sequence | Total number of amino acid residues |
|---|---|---|
| 1 | CSSATGKSC (SEQ ID NO: 1) | 9 |
| 2 | CLAPSPSKC (SEQ ID NO: 2) | 9 |
| 3 | CLGQTKMRC (SEQ ID NO: 3) | 9 |
| 4 | CGHRPYQYC (SEQ ID NO: 4) | 9 |
| 5 | CWAFPLHHC (SEQ ID NO: 5) | 9 |
| 6 | CTLNSHSNC (SEQ ID NO: 6) | 9 |
| 7 | CEISAKRTC (SEQ ID NO: 7) | 9 |
| 8 | CHILHAQAC (SEQ ID NO: 8) | 9 |
| 9 | CPRPPSLEC (SEQ ID NO: 9) | 9 |
| 10 | CTGHWASEC (SEQ ID NO: 10) | 9 |
| 11 | CSYEKRPMC (SEQ ID NO: 11) | 9 |
| 12 | CLTKSYTSC (SEQ ID NO: 12) | 9 |
| 13 | SVSVGMKPSPRP (SEQ ID NO: 13) | 12 |

TABLE 1-continued

| Sample No. | Amino acid sequence | Total number of amino acid residues |
|---|---|---|
| 14 | FTTSNHTSRHGS (SEQ ID NO: 14) | 12 |
| 15 | TPSLPPTMFRLT (SEQ ID NO: 15) | 12 |
| 16 | GPHHYWYHLRLP (SEQ ID NO: 16) | 12 |
| 17 | QSPVNHHYHYHI (SEQ ID NO: 17) | 12 |
| 18 | NMTTYPMHNNTV (SEQ ID NO: 18) | 12 |
| 19 | SLLPHSNHAKHY (SEQ ID NO: 19) | 12 |
| 20 | EFEYFHPATFRL (SEQ ID NO: 20) | 12 |
| 21 | GPHLGMNQRRRP (SEQ ID NO: 21) | 12 |
| 22 | GAVTYSRISGQY (SEQ ID NO: 22) | 12 |

TABLE 2

| Sample No. | Amino acid sequence | Total number of amino acid residues |
|---|---|---|
| 23 | CSSATGKSCKKRTLRKNDRKKR (SEQ ID NO: 23) | 22 |
| 24 | CLAPSPSKCKKRTLRKNDRKKR (SEQ ID NO: 24) | 22 |
| 25 | CLGQTKMRCKKRTLRKNDRKKR (SEQ ID NO: 25) | 22 |
| 26 | CGHRPYQYCKKRTLRKNDRKKR (SEQ ID NO: 26) | 22 |
| 27 | CWAFPLHHCKKRTLRKNDRKKR (SEQ ID NO: 27) | 22 |
| 28 | CTLNSHSNCKKRTLRKNDRKKR (SEQ ID NO: 28) | 22 |
| 29 | CEISAKRTCKKRTLRKNDRKKR (SEQ ID NO: 29) | 22 |
| 30 | CHILHAQACKKRTLRKNDRKKR (SEQ ID NO: 30) | 22 |
| 31 | CPRPPSLECKKRTLRKNDRKKR (SEQ ID NO: 31) | 22 |
| 32 | CTGHWASECKKRTLRKNDRKKR (SEQ ID NO: 32) | 22 |
| 33 | CSYEKRPMCKKRTLRKNDRKKR (SEQ ID NO: 33) | 22 |
| 34 | CLTKSYTSCKKRTLRKNDRKKR (SEQ ID NO: 34) | 22 |
| 35 | SVSVGMKPSPRPKKRTLRKNDRKKR (SEQ ID NO: 35) | 25 |

TABLE 2-continued

| Sample No. | Amino acid sequence | Total number of amino acid residues |
|---|---|---|
| 36 | FTTSNHTSRHGSKKRTLRKNDRKKR (SEQ ID NO: 36) | 25 |
| 37 | TPSLPPTMFRLTKKRTLRKNDRKKR (SEQ ID NO: 37) | 25 |
| 38 | GPHHYWYHLRLPKKRTLRKNDRKKR (SEQ ID NO: 38) | 25 |
| 39 | QSPVNHHYHYHIKKRTLRKNDRKKR (SEQ ID NO: 39) | 25 |
| 40 | NMTTYPMHNNTVKKRTLRKNDRKKR (SEQ ID NO: 40) | 25 |
| 41 | SLLPHSNHAKHYKKRTLRKNDRKKR (SEQ ID NO: 41) | 25 |
| 42 | EFEYFHPATFRLKKRTLRKNDRKKR (SEQ ID NO: 42) | 25 |
| 43 | GPHLGMNQRRRPKKRTLRKNDRKKR (SEQ ID NO: 43) | 25 |
| 44 | GAVTYSRISGQYKKRTLRKNDRKKR (SEQ ID NO: 44) | 25 |

Each sample is constituted to have an amino acid sequence shown in Table 1 or 2 (also in the sequence listing). More specifically, Samples 1 to 12 are peptides capable of acting as FtsA inhibitors (SEQ ID NOs: 1 to 10) or FtsZ inhibitors (SEQ ID NOs: 11 to 12) disclosed in Non-Patent Document 1 or in Non-Patent Document 2; and each one is a synthetic peptide consisting of 9 total amino acid residues, characterized by the N-terminal and C-terminal amino acid residues being cysteine residues.

Samples 13 to 22 are peptides capable of acting as FtsA inhibitors (SEQ ID NOs: 13 to 21) or FtsZ inhibitors (SEQ ID NO: 22) described in Non-Patent Document 1 or in Non-Patent Document 2; and each one is a synthetic peptide consisting of 12 total amino acid residues.

Samples 23 to 44 are synthetic peptides each consisting of 22 total amino acid residues (Samples 23 to 34) or 25 total amino acid residues (Samples 35 to 44), characterized by the amino acid sequence of each peptide of Samples 1 to 22 being coupled at the C-terminal side with the amino acid sequence constituting the NoLS of SEQ ID NO: 23.

All peptides were synthesized by solid-phase synthesis (Fmoc chemistry) using a commercial peptide synthesizer (an Intavis AG system) in accordance with its operation manual. Because the mode of using the peptide synthesizer itself is not distinctive to the present invention, detailed description is omitted here.

Each sample synthesized was dissolved in PBS (phosphate buffered saline) to prepare a stock solution having a peptide concentration of 1 mM.

EXAMPLE 2

Antitumor Activity (Multipolarity-Inducing Activity) Assay 1 for Each Synthetic Peptide Some of the sample peptides obtained in Example 1 were tested for antitumor activity against target cultured tumor cells. Details of the assay are as described below.

As the tumor cells tested, a commercial mouse neuroblastoma cell line (N1E-115) was used. The cell line was cultured beforehand in a DMEM medium (i.e. Dulbecco MEM medium (DMEM medium, a Gibco product) containing 10% fetal bovine serum (FBS, a Gibco product), 2 mM of L-glutamine, 50 unit/mL of penicillin, and 50 µg/mL of streptomycin), and the number of cells per well in a 96-well plate was adjusted to approximately $5 \times 10^3$. The volume of the medium for this was 100 µL per well.

Subsequently, the stock solution of each sample peptide shown in Table 3 was added to each well to a peptide concentration in the well of 50 µM or 100 µM.

After the sample peptides were added as described above, the 96-well plate was placed in a $CO_2$ incubator and cultured without agitation at 37° C. under 5% $CO_2$. At the time of the peptide addition (at the start of treatment) and at 6 hours or 24 hours from the peptide addition and the start of incubation, the viability status of the cultured cells tested was analyzed with a commercial colorimetric assay kit. In particular, to each cell-culturing well, "water-soluble tetrazolium salt (WST-8)" was added as a colorimetric reagent; after two hours of incubation following the addition, the cell culture medium supplied with the colorimetric reagent was collected; and the level of inhibition of cell proliferation was evaluated by colorimetry, measuring the absorbance at a wavelength of 450 nm (values corrected with the absorbance at a wavelength of 620 nm, A450-A620) based on reduction of tetrazolium salt. Based on the absorbance at the time of the sample peptide addition (at the start of treatment), the percent decrease in the absorbance after 6 hours or 24 hours was determined as the cell proliferation inhibition rate (%). The results are shown in Table 3.

TABLE 3

| Sample No. (Concentration) | A450(-A620) | | | Proliferation inhibition rate (%) |
|---|---|---|---|---|
| | Start of treatment | After 6 hers | After 24 hers | |
| 1 (50 µM) | 0.2226 | 0.1361 | — | 38.9 |
| 1 (100 µM) | 0.2454 | 0.1104 | — | 55.0 |
| 1 (50 µM) | 0.5047 | — | 0.1578 | 68.7 |
| 1 (100 µM) | 0.4431 | — | 0.1119 | 74.7 |
| 2 (50 µM) | 0.2614 | 0.2235 | — | 14.5 |
| 2 (100 µM) | 0.2891 | 0.2094 | — | 27.6 |
| 2 (50 µM) | 0.5569 | — | 0.3926 | 29.5 |
| 2 (100 µM) | 0.5245 | — | 0.3764 | 28.2 |
| 6 (50 µM) | 0.2439 | 0.1633 | — | 33.0 |
| 6 (100 µM) | 0.1874 | 0.1345 | — | 28.2 |
| 6 (50 µM) | 0.4362 | — | 0.3083 | 29.3 |
| 6 (100 µM) | 0.4021 | — | 0.2830 | 29.6 |
| 13 (50 µM) | 0.8008 | — | 0.5681 | 29.1 |
| 13 (100 µM) | 0.9437 | — | 0.6422 | 31.9 |
| 16 (50 µM) | 0.8283 | — | 0.6912 | 16.6 |
| 16 (100 µM) | 0.8047 | — | 0.6048 | 24.8 |
| 17 (50 µM) | 0.7869 | — | 0.6019 | 23.5 |
| 17 (100 µM) | 0.7755 | — | 0.5818 | 25.0 |
| 18 (50 µM) | 0.7601 | — | 0.6054 | 20.4 |
| 18 (100 µM) | 0.7658 | — | 0.5999 | 21.7 |
| 20 (50 µM) | 0.7681 | — | 0.5772 | 24.9 |
| 20 (100 µM) | 0.8433 | — | 0.6481 | 23.1 |
| 21 (50 µM) | 0.7643 | — | 0.5284 | 30.9 |
| 21 (100 µM) | 0.8315 | — | 0.5810 | 30.1 |
| 23 (50 µM) | 0.9089 | — | 0.4127 | 54.6 |
| 23 (100 µM) | 0.9388 | — | 0.3841 | 59.1 |
| 24 (50 µM) | 0.9622 | — | 0.3492 | 63.7 |
| 24 (100 µM) | 1.0217 | — | 0.3198 | 68.7 |
| 26 (50 µM) | 0.9354 | — | 0.4550 | 51.4 |
| 26 (100 µM) | 0.940 | — | 0.3643 | 61.2 |
| 38 (50 µM) | 0.8283 | — | 0.4605 | 44.4 |
| 38 (100 µM) | 0.8047 | — | 0.3592 | 55.4 |
| 42 (50 µM) | 0.7892 | — | 0.5145 | 34.8 |
| 42 (100 µM) | 0.7874 | — | 0.4114 | 47.8 |

TABLE 3-continued

| Sample No. (Concentration) | A450(-A620) | | | Proliferation inhibition rate (%) |
|---|---|---|---|---|
| | Start of treatment | After 6 hers | After 24 hers | |
| 43 (50 µM) | 0.7643 | — | 0.4784 | 37.4 |
| 43 (100 µM) | 0.8315 | — | 0.4110 | 50.6 |

As shown in Table 3, each of the sample peptides used in the present example inhibited proliferation of the tumor cells tested (mouse neuroblastoma cell line, N1E-115). In particular, the peptide of Sample 1 and NoLS-coupled peptides of Samples 23, 24, 26, 38, 42 and 43 were found to have high antitumor activity (tumor cell proliferation-inhibiting activity). On the other hand, although details of the results are not presented, the same tests were carried out with human skin fibroblasts (CCD1079sk) and human fetal skin cells (WS-1), mostly resulting in cell proliferation inhibition rates are below 5% (typically below 3%). This indicates that the peptide disclosed herein can induce multipolarity specifically in tumor cells and block or suppress proliferation of the tumor cells (cancer cells).

EXAMPLE 3

Antitumor Activity (Multipolarity-Inducing Activity) Assay 2 for Each Synthetic Peptide HeLa cells (HeLa S3) were substituted for the tumor cells tested and the same test as Example 2 described above was carried out. In the present example, the peptides of Samples 1 to 7, 9, 10, 13, 16, 21 and 35 were used. Table 4 shows the cell proliferation inhibition rates (%) according to Samples 1 to 7, 9 and 10.

TABLE 4

| Sample No. (Concentration) | A450(-A620) | | Proliferation inhibition rate (%) |
|---|---|---|---|
| | Start of treatment | After 24 hers | |
| 1 (50 µM) | 0.1768 | 0.1028 | 42.1 |
| 1 (100 µM) | 0.1712 | 0.0891 | 48.0 |
| 2 (50 µM) | 0.1780 | 0.0924 | 48.1 |
| 2 (100 µM) | 0.1633 | 0.0739 | 54.7 |
| 3 (50 µM) | 0.1606 | 0.1194 | 25.7 |
| 3 (100 µM) | 0.1627 | 0.0997 | 38.7 |
| 4 (50 µM) | 0.1742 | 0.0955 | 45.2 |
| 4 (100 µM) | 0.1697 | 0.0937 | 44.8 |
| 5 (50 µM) | 0.1781 | 0.0955 | 46.4 |
| 5 (100 µM) | 0.1746 | 0.0952 | 45.5 |
| 6 (50 µM) | 0.1810 | 0.1174 | 35.1 |
| 6 (100 µM) | 0.1607 | 0.0906 | 43.6 |
| 7 (50 µM) | 0.1745 | 0.1508 | 13.6 |
| 7 (100 µM) | 0.1691 | 0.1081 | 36.1 |
| 9 (50 µM) | 0.1879 | 0.1366 | 27.3 |
| 9 (100 µM) | 0.1766 | 0.0892 | 49.5 |
| 10 (50 µM) | 0.1761 | 0.0909 | 48.4 |
| 10 (100 µM) | 0.1611 | 0.0915 | 43.2 |

As shown in Table 4, each of peptides of Samples 1 to 7, 9 and 10 used in the present example inhibited proliferation of the tumor cells tested (HeLa cells).

Figure 2:
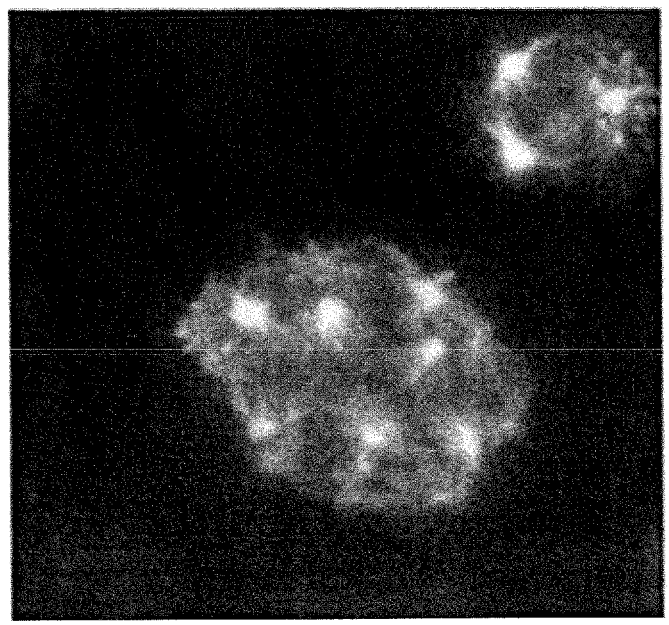
FIG. 2 is a fluorescence microscope photo (image) showing the state of cultured cells after 24 hours of incubation following addition of a sample peptide (Sample 9) to a culture medium of HeLa cells to a peptide concentration in the culture medium of 50 with the photo being a merged image of a DAPI nuclear stain image and a fluorescence image showing the result of an immunofluorescence assay using a fluorescence-labeled anti-tubulin antibody.
Figure 3:
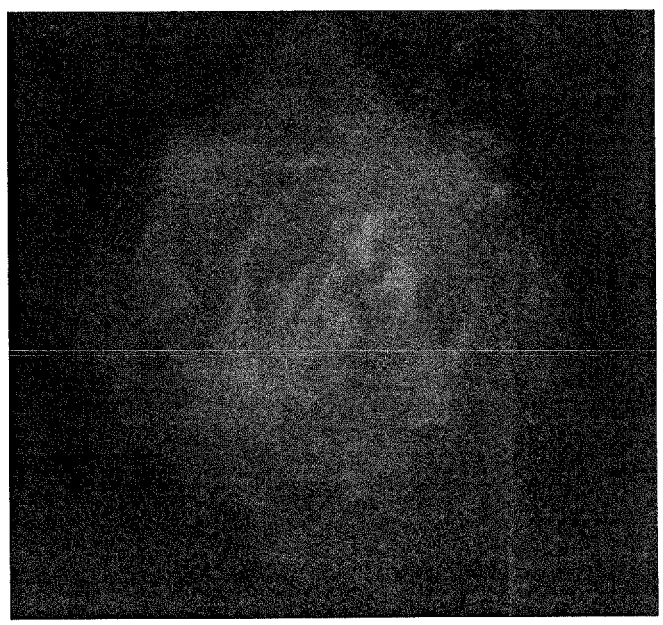
FIG. 3 is a fluorescence microscope photo (image) showing the state of a cultured cell after 24 hours of incubation following addition of a sample peptide (Sample 13) to a culture medium of HeLa cells to a peptide concentration in the culture medium of 100 µM, with the photo being a merged image of a DAPI nuclear stain image and a fluorescence image showing the result of an immunofluorescence assay using a fluorescence-labeled anti-tubulin antibody.
Figure 4:
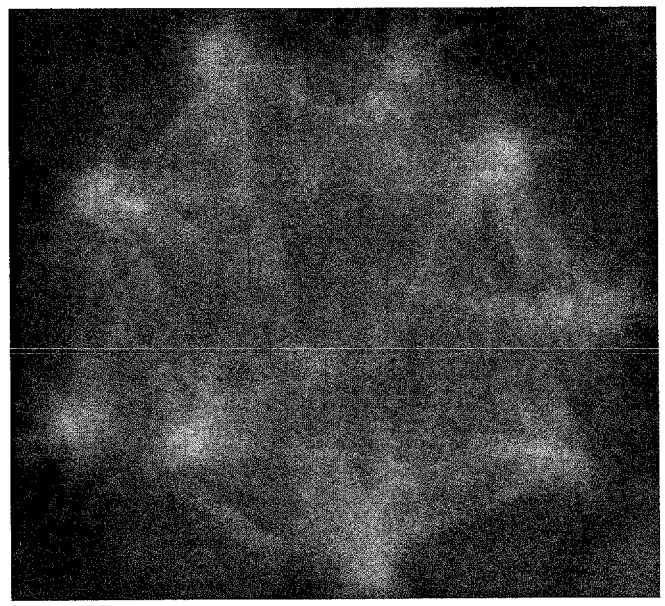
FIG. 4 is a fluorescence microscope photo (image) showing the state of a cultured cell after 24 hours of incubation following addition of a sample peptide (Sample 16) to a culture medium of HeLa cells to a peptide concentration in the culture medium of 100 µM, with the photo being a merged image of a DAPI nuclear stain image and a fluorescence image showing the result of an immunofluorescence assay using a fluorescence-labeled anti-tubulin antibody.
Figure 5:
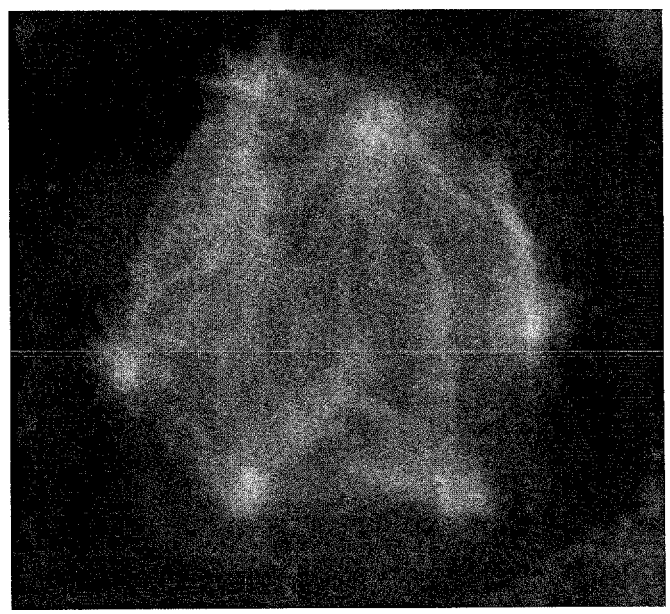
FIG. 5 is a fluorescence microscope photo (image) showing the state of a cultured cell after 24 hours of incubation following addition of a sample peptide (Sample 21) to a culture medium of HeLa cells to a peptide concentration in the culture medium of 100 µM, with the photo being a merged image of a DAPI nuclear stain image and a fluorescence image showing the result of an immunofluorescence assay using a fluorescence-labeled anti-tubulin antibody.
Figure 6:
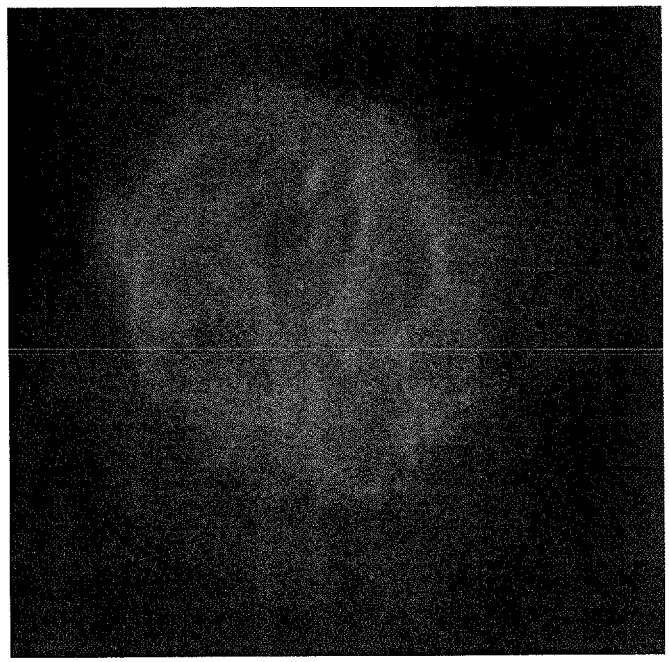
FIG. 6 is a fluorescence microscope photo (image) showing the state of a cultured cell after 24 hours of incubation following addition of a sample peptide (Sample 35) to a culture medium of HeLa cells to a peptide concentration in the culture medium of 100 µM, with the photo being a merged image of a DAPI nuclear stain image and a fluorescence image showing the result of an immunofluorescence assay using a fluorescence-labeled anti-tubulin antibody.

In addition, the cultured cells supplemented with the peptides were observed under fluorescence microscope. Herein, as for some examples, the observations on Samples 1, 9, 13, 16, 21 and 35 are outlined. In particular, each peptide was added to a peptide concentration in a well of 50 µM (Samples 1, 9) or 100 µM (Samples 13, 16, 21, 35). After 24 hours, the cultured cells were subjected to nuclear staining with DAPI (4',6-diamidino-2-phenylindole) and observed under fluorescence microscope. As a marker for spindles, α-tubulin was used; and the cells were tested for the presence of tubulin (i.e. the presence of spindles) by immunofluorescence, using a fluorescence-labeled anti-tubulin antibody to identify the tubulin. FIGS. 1 to 6 show merged images of DAPI-stained images and fluorescence images showing the results of the immunofluorescence assays using the fluorescence-labeled anti-tubulin antibody.

As shown in the respective images, in the culture media each incubated with addition of one of the peptides of Sample 1 (FIG. 1), Sample 9 (FIG. 2), Sample 13 (FIG. 3), Sample 16 (FIG. 4), Sample 21 (FIG. 5) and Sample 35 (FIG. 6), formation of multipolar spindles, that is, the presence of many multipolar cells (HeLa cells herein) was confirmed as indicated by the images.

EXAMPLE 4

Antitumor Activity (Multipolarity-Inducing Activity) Assay 3 for Each Synthetic Peptide Cells forming a squamous cell carcinoma (human alveolar basal epithelial adenocarcinoma cells, A549) were substituted for the tumor cells tested and the same test as Example 2 described above was carried out. In the present example, the peptides of Samples 1 to 13, 15 to 22, 24, 29, 35 and 40 were used. The results are shown in Table 5.

TABLE 5

| Sample No. (Concentration) | A450(-A620) Start of treatment | After 24 hers | Proliferation inhibition rate (%) |
| --- | --- | --- | --- |
| 1 (50 μM) | 2.5812 | 1.5487 | 40.0 |
| 2 (50 μM) | 2.4896 | 1.8971 | 23.8 |
| 3 (50 μM) | 2.6108 | 1.7022 | 34.8 |
| 4 (50 μM) | 2.3614 | 1.7663 | 25.2 |
| 5 (50 μM) | 2.6980 | 1.8994 | 29.6 |
| 6 (50 μM) | 2.2496 | 1.4667 | 34.8 |
| 7 (50 μM) | 2.2549 | 1.6822 | 25.4 |
| 8 (50 μM) | 2.2440 | 1.7885 | 20.3 |
| 9 (50 μM) | 2.4630 | 1.8645 | 24.3 |
| 10 (50 μM) | 2.3265 | 1.7472 | 24.9 |
| 11 (50 μM) | 2.5996 | 1.6741 | 35.6 |
| 12 (50 μM) | 2.5351 | 1.9165 | 24.4 |
| 13 (50 μM) | 2.5711 | 1.9412 | 24.5 |
| 15 (50 μM) | 2.2346 | 1.6022 | 28.3 |
| 16 (50 μM) | 2.3517 | 1.7309 | 26.4 |
| 17 (50 μM) | 2.4655 | 1.9428 | 21.2 |
| 18 (50 μM) | 2.3582 | 1.6767 | 28.9 |
| 19 (50 μM) | 2.3070 | 1.8271 | 20.8 |
| 20 (50 μM) | 2.4251 | 1.8115 | 25.3 |
| 21 (50 μM) | 2.3184 | 1.5672 | 32.4 |
| 22 (50 μM) | 2.5467 | 1.9711 | 22.6 |
| 24 (50 μM) | 2.5682 | 1.5820 | 38.4 |
| 29 (50 μM) | 2.5193 | 1.6577 | 34.2 |
| 35 (50 μM) | 2.5513 | 1.7451 | 31.6 |
| 40 (50 μM) | 2.5302 | 1.5890 | 37.2 |

As shown in Table 5, each of the sample peptides used in the present example inhibited proliferation of the tumor cells tested (human alveolar basal epithelial adenocarcinoma cells, A549). In particular, the peptides of Samples 1, 3, 6, 11 and 21 and NoLS-coupled peptides of Samples 24, 29, 35 and 40 were found to have high antitumor activity (tumor cell proliferation-inhibiting activity). This indicates that the peptide disclosed herein can induce multipolarity in tumor cells that may occur in humans and block or suppress proliferation of the tumor cells (cancer cells).

INDUSTRIAL APPLICABILITY

As described above, according to the antitumor peptide disclosed herein, multipolarity can be induced frequently in tumor cells and proliferation of the tumor cells can be inhibited or suppressed. Thus, the use of the antitumor peptide provided by the present invention can provide an antitumor composition (antitumor drug) to inhibit or suppress proliferation of tumor cells.

SEQUENCE LISTING FREE TEXT

SEQ ID NOs: 1 to 22, 31 to 52 synthetic peptides

SEQUENCE LISTING

TG 12-006PCT_ST25.txt

The invention claimed is:

1. A method for suppressing proliferation of at least one species of tumor cells selected from the group consisting of cervical tumor cells, breast tumor cells, prostate tumor cells, and tumor cells forming a squamous cell carcinoma or an adenocarcinoma, the method comprising supplying a composition comprising an antitumor peptide and a pharmaceutically acceptable carrier to target the tumor cells in vitro at least once, wherein the antitumor peptide consists of an amino acid sequence selected from the group consisting of: CSSATGKSC (SEQ ID NO: 1), CLAPSPSKC (SEQ ID NO: 2), CLGQTKMRC (SEQ ID NO: 3), CGHRPYQYC (SEQ ID NO: 4), CWAFPLHHC (SEQ ID NO: 5), CTLNSHSNC (SEQ ID NO: 6), CEISAKRTC (SEQ ID NO: 7), CHILHAQAC (SEQ ID NO: 8), CPRPPSLEC (SEQ ID NO: 9), CTGHWASEC (SEQ ID NO: 10), CSYEKRPMC (SEQ ID NO: 11), CLTKSYTSC (SEQ ID NO: 12), FTTSNHTSRHGS (SEQ ID NO: 14), TPSLPPTMFRLT (SEQ ID NO: 15), GPHHYWYHLRLP (SEQ ID NO: 16), QSPVNHHYHYHI (SEQ ID NO: 17), NMTTYPMHNNTV (SEQ ID NO: 18), SLLPHSNHAKHY (SEQ ID NO: 19), EFEYFHPATFRL (SEQ ID NO: 20), GPHLGMNQRRRP (SEQ ID NO: 21) and GAVTYSRISGQY (SEQ ID NO: 22).

2. The method according to claim 1, wherein the tumor cells are cells forming a squamous cell carcinoma or an adenocarcinoma.

* * * * *

SEQUENCE LISTING

<160> NUMBER OF SEQ ID NOS: 52

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1

Cys Ser Ser Ala Thr Gly Lys Ser Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide

```
<400> SEQUENCE: 2

Cys Leu Ala Pro Ser Pro Ser Lys Cys
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Cys Leu Gly Gln Thr Lys Met Arg Cys
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Cys Gly His Arg Pro Tyr Gln Tyr Cys
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Cys Trp Ala Phe Pro Leu His His Cys
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Cys Thr Leu Asn Ser His Ser Asn Cys
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7

Cys Glu Ile Ser Ala Lys Arg Thr Cys
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 8

Cys His Ile Leu His Ala Gln Ala Cys
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Cys Pro Arg Pro Pro Ser Leu Glu Cys
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

Cys Thr Gly His Trp Ala Ser Glu Cys
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Cys Ser Tyr Glu Lys Arg Pro Met Cys
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Cys Leu Thr Lys Ser Tyr Thr Ser Cys
1               5

<210> SEQ ID NO 13
<211> LENGTH: 12
<212> TYPE: PRT
<213> ORGANISM: Artificial sequence
<220> FEATURE:
<223> OTHER INFORMATION: Synthetic peptide

<400> SEQUENCE: 13

Ser Val Ser Val Gly Met Lys Pro Ser Pro Arg Pro
1               5                   10

<210> SEQ ID NO 14
<211> LENGTH: 12
<212> TYPE: PRT
<213> ORGANISM: Artificial sequence
<220> FEATURE:
<223> OTHER INFORMATION: Synthetic peptide

<400> SEQUENCE: 14
```

```
Phe Thr Thr Ser Asn His Thr Ser Arg His Gly Ser
1               5                   10
```

<210> SEQ ID NO 15
<211> LENGTH: 12
<212> TYPE: PRT
<213> ORGANISM: Artificial sequence
<220> FEATURE:
<223> OTHER INFORMATION: Synthetic peptide

<400> SEQUENCE: 15

```
Thr Pro Ser Leu Pro Pro Thr Met Phe Arg Leu Thr
1               5                   10
```

<210> SEQ ID NO 16
<211> LENGTH: 12
<212> TYPE: PRT
<213> ORGANISM: Artificial sequence
<220> FEATURE:
<223> OTHER INFORMATION: Synthetic peptide

<400> SEQUENCE: 16

```
Gly Pro His His Tyr Trp Tyr His Leu Arg Leu Pro
1               5                   10
```

<210> SEQ ID NO 17
<211> LENGTH: 12
<212> TYPE: PRT
<213> ORGANISM: Artificial sequence
<220> FEATURE:
<223> OTHER INFORMATION: Synthetic peptide

<400> SEQUENCE: 17

```
Gln Ser Pro Val Asn His His Tyr His Tyr His Ile
1               5                   10
```

<210> SEQ ID NO 18
<211> LENGTH: 12
<212> TYPE: PRT
<213> ORGANISM: Artificial sequence
<220> FEATURE:
<223> OTHER INFORMATION: Synthetic peptide

<400> SEQUENCE: 18

```
Asn Met Thr Thr Tyr Pro Met His Asn Asn Thr Val
1               5                   10
```

<210> SEQ ID NO 19
<211> LENGTH: 12
<212> TYPE: PRT
<213> ORGANISM: Artificial sequence
<220> FEATURE:
<223> OTHER INFORMATION: Synthetic peptide

<400> SEQUENCE: 19

```
Ser Leu Leu Pro His Ser Asn His Ala Lys His Tyr
1               5                   10
```

<210> SEQ ID NO 20
<211> LENGTH: 12
<212> TYPE: PRT
<213> ORGANISM: Artificial sequence
<220> FEATURE:
<223> OTHER INFORMATION: Synthetic peptide

<400> SEQUENCE: 20

```
Glu Phe Glu Tyr Phe His Pro Ala Thr Phe Arg Leu
1               5                   10
```

<210> SEQ ID NO 21
<211> LENGTH: 12
<212> TYPE: PRT
<213> ORGANISM: Artificial sequence
<220> FEATURE:
<223> OTHER INFORMATION: Synthetic peptide

<400> SEQUENCE: 21

```
Gly Pro His Leu Gly Met Asn Gln Arg Arg Arg Pro
1               5                   10
```

<210> SEQ ID NO 22
<211> LENGTH: 12
<212> TYPE: PRT
<213> ORGANISM: Artificial sequence
<220> FEATURE:
<223> OTHER INFORMATION: Synthetic peptide

<400> SEQUENCE: 22

```
Gly Ala Val Thr Tyr Ser Arg Ile Ser Gly Gln Tyr
1               5                   10
```

<210> SEQ ID NO 23
<211> LENGTH: 13
<212> TYPE: PRT
<213> ORGANISM: Homo sapiens
<220> FEATURE:

<400> SEQUENCE: 23

```
Lys Lys Arg Thr Leu Arg Lys Asn Asp Arg Lys Lys Arg
1               5                   10
```

<210> SEQ ID NO 24
<211> LENGTH: 8
<212> TYPE: PRT
<213> ORGANISM: Avian infectious bronchitis virus
<220> FEATURE:

<400> SEQUENCE: 24

```
Trp Arg Arg Gln Ala Arg Phe Lys
1               5
```

<210> SEQ ID NO 25
<211> LENGTH: 14
<212> TYPE: PRT
<213> ORGANISM: Homo sapiens
<220> FEATURE:

<400> SEQUENCE: 25

```
Arg Ser Arg Lys Tyr Thr Ser Trp Tyr Val Ala Leu Lys Arg
1               5                   10
```

<210> SEQ ID NO 26
<211> LENGTH: 19
<212> TYPE: PRT
<213> ORGANISM: Homo sapiens
<220> FEATURE:

<400> SEQUENCE: 26

```
Met Ala Lys Ser Ile Arg Ser Lys His Arg Arg Gln Met Arg Met Met
1               5                   10                  15

Lys Arg Glu
```

```
<210> SEQ ID NO 27
<211> LENGTH: 16
<212> TYPE: PRT
<213> ORGANISM: herpes simplex virus 1
<220> FEATURE:

<400> SEQUENCE: 27

Met Ala Arg Arg Arg His Arg Gly Pro Arg Arg Pro Arg Pro Pro
1               5                   10                  15

<210> SEQ ID NO 28
<211> LENGTH: 19
<212> TYPE: PRT
<213> ORGANISM: Homo sapiens
<220> FEATURE:

<400> SEQUENCE: 28

Gly Arg Cys Arg Arg Leu Ala Asn Phe Gly Pro Arg Lys Arg Arg
1               5                   10                  15

Arg Arg Arg

<210> SEQ ID NO 29
<211> LENGTH: 16
<212> TYPE: PRT
<213> ORGANISM: Marek's disease gammaherpesvirus MKT-1
<220> FEATURE:

<400> SEQUENCE: 29

Arg Arg Arg Lys Arg Asn Arg Asp Ala Arg Arg Arg Arg Lys Gln
1               5                   10                  15

<210> SEQ ID NO 30
<211> LENGTH: 17
<212> TYPE: PRT
<213> ORGANISM: Homo sapiens
<220> FEATURE:

<400> SEQUENCE: 30

Met Gln Arg Lys Pro Thr Ile Arg Arg Lys Asn Leu Arg Leu Arg Arg
1               5                   10                  15

Lys

<210> SEQ ID NO 31
<211> LENGTH: 22
<212> TYPE: PRT
<213> ORGANISM: Artificial Sequence
<220> FEATURE:
<223> OTHER INFORMATION: Synthetic peptide
<220> FEATURE:

<400> SEQUENCE: 31

Cys Ser Ser Ala Thr Gly Lys Ser Cys Lys Lys Arg Thr Leu Arg Lys
1               5                   10                  15

Asn Asp Arg Lys Lys Arg
            20

<210> SEQ ID NO 32
<211> LENGTH: 22
<212> TYPE: PRT
<213> ORGANISM: Artificial Sequence
<220> FEATURE:
<223> OTHER INFORMATION: Synthetic peptide

<400> SEQUENCE: 32
```

Cys Leu Ala Pro Ser Pro Ser Lys Cys Lys Arg Thr Leu Arg Lys
1               5                   10                  15

Asn Asp Arg Lys Lys Arg
            20

<210> SEQ ID NO 33
<211> LENGTH: 22
<212> TYPE: PRT
<213> ORGANISM: Artificial Sequence
<220> FEATURE:
<223> OTHER INFORMATION: Synthetic peptide

<400> SEQUENCE: 33

Cys Leu Gly Gln Thr Lys Met Arg Cys Lys Arg Thr Leu Arg Lys
1               5                   10                  15

Asn Asp Arg Lys Lys Arg
            20

<210> SEQ ID NO 34
<211> LENGTH: 22
<212> TYPE: PRT
<213> ORGANISM: Artificial Sequence
<220> FEATURE:
<223> OTHER INFORMATION: Synthetic peptide

<400> SEQUENCE: 34

Cys Gly His Arg Pro Tyr Gln Tyr Cys Lys Arg Thr Leu Arg Lys
1               5                   10                  15

Asn Asp Arg Lys Lys Arg
            20

<210> SEQ ID NO 35
<211> LENGTH: 22
<212> TYPE: PRT
<213> ORGANISM: Artificial Sequence
<220> FEATURE:
<223> OTHER INFORMATION: Synthetic peptide

<400> SEQUENCE: 35

Cys Trp Ala Phe Pro Leu His His Cys Lys Arg Thr Leu Arg Lys
1               5                   10                  15

Asn Asp Arg Lys Lys Arg
            20

<210> SEQ ID NO 36
<211> LENGTH: 22
<212> TYPE: PRT
<213> ORGANISM: Artificial Sequence
<220> FEATURE:
<223> OTHER INFORMATION: Synthetic peptide

<400> SEQUENCE: 36

Cys Thr Leu Asn Ser His Ser Asn Cys Lys Arg Thr Leu Arg Lys
1               5                   10                  15

Asn Asp Arg Lys Lys Arg
            20

<210> SEQ ID NO 37
<211> LENGTH: 22
<212> TYPE: PRT
<213> ORGANISM: Artificial Sequence
<220> FEATURE:
<223> OTHER INFORMATION: Synthetic peptide

<400> SEQUENCE: 37

Cys Glu Ile Ser Ala Lys Arg Thr Cys Lys Lys Arg Thr Leu Arg Lys
1               5                   10                  15

Asn Asp Arg Lys Lys Arg
            20

<210> SEQ ID NO 38
<211> LENGTH: 22
<212> TYPE: PRT
<213> ORGANISM: Artificial Sequence
<220> FEATURE:
<223> OTHER INFORMATION: Synthetic peptide

<400> SEQUENCE: 38

Cys His Ile Leu His Ala Gln Ala Cys Lys Lys Arg Thr Leu Arg Lys
1               5                   10                  15

Asn Asp Arg Lys Lys Arg
            20

<210> SEQ ID NO 39
<211> LENGTH: 22
<212> TYPE: PRT
<213> ORGANISM: Artificial Sequence
<220> FEATURE:
<223> OTHER INFORMATION: Synthetic peptide

<400> SEQUENCE: 39

Cys Pro Arg Pro Pro Ser Leu Glu Cys Lys Lys Arg Thr Leu Arg Lys
1               5                   10                  15

Asn Asp Arg Lys Lys Arg
            20

<210> SEQ ID NO 40
<211> LENGTH: 22
<212> TYPE: PRT
<213> ORGANISM: Artificial Sequence
<220> FEATURE:
<223> OTHER INFORMATION: Synthetic peptide

<400> SEQUENCE: 40

Cys Thr Gly His Trp Ala Ser Glu Cys Lys Lys Arg Thr Leu Arg Lys
1               5                   10                  15

Asn Asp Arg Lys Lys Arg
            20

<210> SEQ ID NO 41
<211> LENGTH: 22
<212> TYPE: PRT
<213> ORGANISM: Artificial Sequence
<220> FEATURE:
<223> OTHER INFORMATION: Synthetic peptide

<400> SEQUENCE: 41

Cys Ser Tyr Glu Lys Arg Pro Met Cys Lys Lys Arg Thr Leu Arg Lys
1               5                   10                  15

Asn Asp Arg Lys Lys Arg
            20

<210> SEQ ID NO 42
<211> LENGTH: 22
<212> TYPE: PRT
<213> ORGANISM: Artificial Sequence
<220> FEATURE:
<223> OTHER INFORMATION: Synthetic peptide

<400> SEQUENCE: 42

Cys Leu Thr Lys Ser Tyr Thr Ser Cys Lys Lys Arg Thr Leu Arg Lys
1               5                   10                  15

Asn Asp Arg Lys Lys Arg
            20

<210> SEQ ID NO 43
<211> LENGTH: 25
<212> TYPE: PRT
<213> ORGANISM: Artificial sequence
<220> FEATURE:
<223> OTHER INFORMATION: Synthetic peptide

<400> SEQUENCE: 43

Ser Val Ser Val Gly Met Lys Pro Ser Pro Arg Pro Lys Lys Arg Thr
1               5                   10                  15

Leu Arg Lys Asn Asp Arg Lys Lys Arg
            20                  25

<210> SEQ ID NO 44
<211> LENGTH: 25
<212> TYPE: PRT
<213> ORGANISM: Artificial sequence
<220> FEATURE:
<223> OTHER INFORMATION: Synthetic peptide

<400> SEQUENCE: 44

Phe Thr Thr Ser Asn His Thr Ser Arg His Gly Ser Lys Lys Arg Thr
1               5                   10                  15

Leu Arg Lys Asn Asp Arg Lys Lys Arg
            20                  25

<210> SEQ ID NO 45
<211> LENGTH: 25
<212> TYPE: PRT
<213> ORGANISM: Artificial sequence
<220> FEATURE:
<223> OTHER INFORMATION: Synthetic peptide

<400> SEQUENCE: 45

Thr Pro Ser Leu Pro Pro Thr Met Phe Arg Leu Thr Lys Lys Arg Thr
1               5                   10                  15

Leu Arg Lys Asn Asp Arg Lys Lys Arg
            20                  25

<210> SEQ ID NO 46
<211> LENGTH: 25
<212> TYPE: PRT
<213> ORGANISM: Artificial sequence
<220> FEATURE:
<223> OTHER INFORMATION: Synthetic peptide

<400> SEQUENCE: 46

Gly Pro His His Tyr Trp Tyr His Leu Arg Leu Pro Lys Lys Arg Thr
1               5                   10                  15

Leu Arg Lys Asn Asp Arg Lys Lys Arg
            20                  25

<210> SEQ ID NO 47
<211> LENGTH: 25
<212> TYPE: PRT
<213> ORGANISM: Artificial sequence
<220> FEATURE:
<223> OTHER INFORMATION: Synthetic peptide -continued

```
<400> SEQUENCE: 47

Gln Ser Pro Val Asn His His Tyr His Tyr His Ile Lys Lys Arg Thr
1               5                   10                  15

Leu Arg Lys Asn Asp Arg Lys Lys Arg
            20                  25

<210> SEQ ID NO 48
<211> LENGTH: 25
<212> TYPE: PRT
<213> ORGANISM: Artificial sequence
<220> FEATURE:
<223> OTHER INFORMATION: Synthetic peptide

<400> SEQUENCE: 48

Asn Met Thr Thr Tyr Pro Met His Asn Asn Thr Val Lys Lys Arg Thr
1               5                   10                  15

Leu Arg Lys Asn Asp Arg Lys Lys Arg
            20                  25

<210> SEQ ID NO 49
<211> LENGTH: 25
<212> TYPE: PRT
<213> ORGANISM: Artificial sequence
<220> FEATURE:
<223> OTHER INFORMATION: Synthetic peptide

<400> SEQUENCE: 49

Ser Leu Leu Pro His Ser Asn His Ala Lys His Tyr Lys Lys Arg Thr
1               5                   10                  15

Leu Arg Lys Asn Asp Arg Lys Lys Arg
            20                  25

<210> SEQ ID NO 50
<211> LENGTH: 25
<212> TYPE: PRT
<213> ORGANISM: Artificial sequence
<220> FEATURE:
<223> OTHER INFORMATION: Synthetic peptide

<400> SEQUENCE: 50

Glu Phe Glu Tyr Phe His Pro Ala Thr Phe Arg Leu Lys Lys Arg Thr
1               5                   10                  15

Leu Arg Lys Asn Asp Arg Lys Lys Arg
            20                  25

<210> SEQ ID NO 51
<211> LENGTH: 25
<212> TYPE: PRT
<213> ORGANISM: Artificial sequence
<220> FEATURE:
<223> OTHER INFORMATION: Synthetic peptide

<400> SEQUENCE: 51

Gly Pro His Leu Gly Met Asn Gln Arg Arg Pro Lys Lys Arg Thr
1               5                   10                  15

Leu Arg Lys Asn Asp Arg Lys Lys Arg
            20                  25

<210> SEQ ID NO 52
<211> LENGTH: 25
<212> TYPE: PRT
<213> ORGANISM: Artificial sequence
<220> FEATURE:
```

<223> OTHER INFORMATION: Synthetic peptide

<400> SEQUENCE: 52

```
Gly Ala Val Thr Tyr Ser Arg Ile Ser Gly Gln Tyr Lys Lys Arg Thr
1               5                   10                  15

Leu Arg Lys Asn Asp Arg Lys Lys Arg
            20                  25
```